(12) United States Patent
Karimian et al.

(10) Patent No.: US 6,245,903 B1
(45) Date of Patent: Jun. 12, 2001

(54) AZITHROMYCIN MONOHYDRATE ISOPROPANOL CLATHRATE AND METHODS FOR THE MANUFACTURE THEREOF

(75) Inventors: Khashayar Karimian, Mississauga (CA); Mehrnoush Motamedi, San Diego, CA (US)

(73) Assignee: Apotex, Inc., Weston (CA)

( * ) Notice: Subject to any disclaimer, the term of this patent is extended or adjusted under 35 U.S.C. 154(b) by 0 days.

(21) Appl. No.: 09/373,549

(22) Filed: Aug. 13, 1999

(30) Foreign Application Priority Data

Aug. 21, 1998 (CA) .................................................. 2245398

(51) Int. Cl.⁷ ............................. C07H 17/08; C07H 1/00
(52) U.S. Cl. ........................................... 536/7.4; 536/18.5
(58) Field of Search ...................................... 536/7.4, 18.5

(56) References Cited

FOREIGN PATENT DOCUMENTS

| | | |
|---|---|---|
| 1191843 | 8/1985 | (CA) . |
| 1202619 | 4/1986 | (CA) . |
| 1202626 | 4/1986 | (CA) . |
| 1202963 | 4/1986 | (CA) . |
| 1314876 | 7/1988 | (CA) . |
| 0 298 650 | 1/1992 | (EP) . |

OTHER PUBLICATIONS

*Federal Register*, vol. 62, No. 247, 67381, Dec. 25, 1997.

*Primary Examiner*—Elli Peselev
(74) *Attorney, Agent, or Firm*—Nixon & Vanderhye P.C.

(57) ABSTRACT

A novel form of azithromycin and processes for preparation of pure azithromycin monohydrate isopropanol clathrate (3 molecules of isopropanol for every 10 molecules of azithromycin monohydrate) has been obtained. Preparation of the novel form of azithromycin comprises the steps of dissolving azithromycin in isopropanol, followed by the slow addition of water to the organic solution.

9 Claims, 7 Drawing Sheets

AZITHROMYCIN MONOHYDRATE ISOPROPANOL CLATHRATE AND METHODS FOR THE MANUFACTURE THEREOF

FIELD OF THE INVENTION

This invention relates to a new form of azithromycin, namely azithromycin monohydrate isopropanol clathrate, which has improved properties over amorphous azithromycin, azithromycin monohydrate and azithromycin dihydrate. This invention also relates processes for the manufacture of azithromycin monohydrate isopropanol clathrate.

BACKGROUND OF THE INVENTION

Azithromycin, 9-Deoxo-9a-aza-9a-methyl-9a-homoerythromycin A, is a semi-synthetic macrolide antibiotic which can be classified as a member of the second-generation erythromycin antibacterial agent. Azithromycin has the following structure (I):

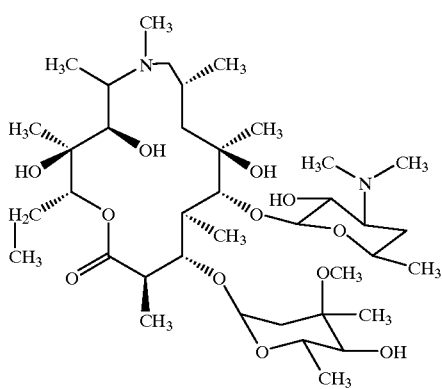

(I)

The spectrum of azithromycin's antibacterial activity has been reported by Aronoff, et al (*J. Antimicrob. Chemother.*, 1987, 19, 275). Its mode of action has been reviewed by Retsema, et al (*Antimicrob. Ag. Chemother.*, 1987, 31, 1939)n, and its pharmacology has been reviewed by a number of investigators (*J. Antimicrob. Chemother.*, 1993, 31, Suppl. E, 1–198).

Three forms of Azithromycin are known. Anhydrous azithromycin is reported as an amorphous crude product (foam) in Canadian Patent 1 191 843 (example 1). It is obtained by evaporating the final solvent (e.g. chloroform) used in the process of preparation of azithromycin. It is not a crystalline product and therefore can not be made in pure form per se in commercial scale. In laboratory scale, it can be obtained in pure form by chromatography of the crude final product or by dissolving pure crystalline azithromycin mono- or dihydrate in an organic solvent and evaporating the said solvent to obtain amorphous anhydrous azithromycin.

Canadian patents 1,202,620, 1,202,619, 1,202,963 and 1,314,876 teach the process of making azithromycin monohydrate but do not claim the resulting product. Furthermore, these patents do not provide a description of the drying process (temperature or pressure). Canadian patents 1,191, 843 and 1,202,963 claim azithromycin monohydrate as a new form of azithromycin. The theoretical percentage of water in azithromycin monohydrate is 2.3%. However, Canadian Patent 1,314,876 reports a value of 3.92%, and a value of 3.2% is reported in Canadian patent 1,314,876. No reference to the percentage of water is made in the other above-mentioned Canadian patents. Azithromycin monohydrate is known to be hygroscopic (see for example European Patent 298 650 B1). This is an undesirable property since it complicates formulation of azithromycin drug product and can adversely effect its stability on long term storage.

Canadian patent 1,314,876 claims azithromycin dihydrate and, in contrast to azithromycin monohydrate, a full description of the drying process used for obtaining the product is provided. Low boiling solvents (tetrahydrofuran and hexane) are used with 3–4 equivalent moles of water to obtain the crystalline product, which is dried under vacuum at low temperatures (20–40° C.). The use of low boiling solvents for crystallisation and low temperatures for vacuum drying of the product are prescribed presumably to control the desirable amount of water that must be evaporated to afford azithromycin dihydrate. Excess loss of water, caused by higher temperature vacuum drying, could result in the formation of azithromycin monohydrate. In contrast to anhydrous azithromycin and azithromycin monohydrate, azithromycin dihydrate has desirable properties for formulation. It is crystalline and can therefore be obtained in pure form in commercial scale. It is not hygroscopic and therefore does not pose a problem during formulation or adversely effect the stability of the resulting drug product.

It is clear that anhydrous and monohydrate forms of azithromycin are not suitable for formulation. The processes referred to in Canadian Patent 1 314 876 for the preparation of azithromycin dihydrate, while producing a non-hygroscopic form of azithromycin, have a number of disadvantages:

1. Water immiscibility of the organic solvent mixture (tetrahydrofuran plus hexane) can cause problems in obtaining pure material since crystallisation processes are known to afford pure material when the anti-solvent is miscible with the solvent used to dissolve the crude product.

2. The drying process must be very carefully controlled since an increase in temperature will cause the transformation of the non-hygroscopic dihydrate to the hygroscopic monohydrate.

3. The use of low boiling point solvents is complicated by their toxicity and possibility of formation of explosive peroxide during solvent recovery.

It has now been surprisingly found that slow addition of water to an isopropanol solution of azithromycin results in the formation of a new form of azithromycin, namely azithromycin monohydrate isopropanol clathrate of formula II:

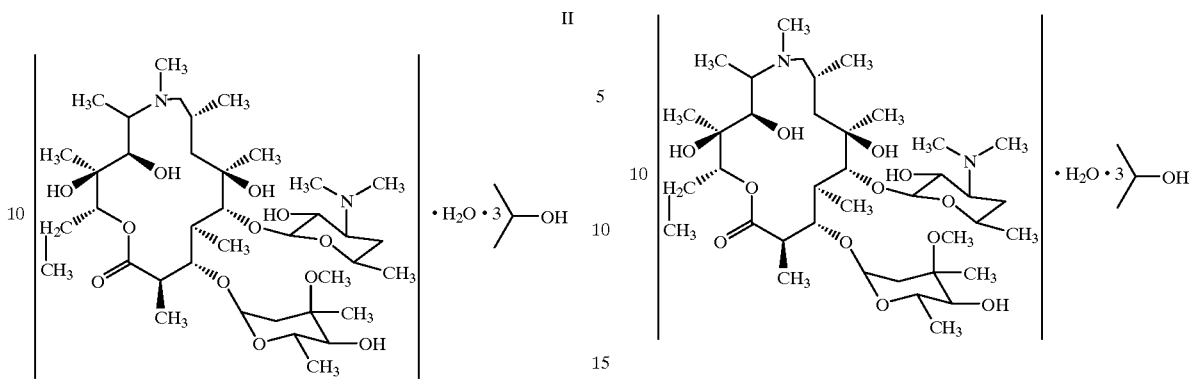

The physical properties of this product and the processes used for its preparation have a number of major advantages over the existing azithromycin product forms and the procedures used for their preparation.

First, azithromycin monohydrate isopropanol clathrate is crystalline and, in contrast to anhydrous azithromycin, may be obtained in pure form.

Second, azithromycin monohydrate isopropanol clathrate is not hygroscopic and, in contrast to anhydrous azithromycin and azithromycin monohydrate, may be used in formulations of the drug product as tablets or capsules with excellent stability profiles.

Third, azithromycin monohydrate isopropanol clathrate is, in contrast to azithromycin dihydrate, obtained conveniently and reproducibly by crystallisation from isopropanol water.

Fourth, in contrast to azithromycin dihydrate, azithromycin monohydrate isopropanol clathrate is obtained by crystallisation from inexpensive solvents.

Fifth, in contrast to azithromycin dihydrate, azithromycin monohydrate isopropanol clathrate is prepared from environmentally safe solvents (hexane: Class 2; isopropanol and tetrahydrofuran: Class 3, see Federal Register, Vol. 62, No. 247, 67381, Dec. 24, 1997).

Sixth, the experimental conditions are simple and applicable to large-scale production.

Seventh, the present processes are reproducible in a wide spectrum of physical conditions and consistently afford azithromycin monohydrate isopropanol clathrate with a constant ratio of azithromycin, water and isopropanol (vacuum drying at 1–10 mm Hg at 500 to 60° C. for 12 to 24 hours).

Eighth, the product generated by the processes of the present invention is highly pure.

Ninth, the processes taught in this invention afford high yields of the product within the range of 88% to 93% (first crop). The remainder of the product is conveniently recovered from the mother liquor by evaporation of isopropanol under reduced pressure.

BRIEF DESCRIPTION OF THE INVENTION

In one aspect, the invention relates to a compound of formula II:

In another aspect, the invention relates to a process for the preparation of azithromycin monohydrate isopropanol clathrate which comprises the steps of:

(a) Dissolving azithromycin in isopropanol and slowly adding water to the resulting solution;

(b) Filtering and washing the product with a mixture of isopropanol water;

(c) Vacuum drying the product.

DETAILED DESCRIPTION OF THE INVENTION

The present invention describes a new form of azithromycin monohydrate, namely azithromycin monohydrate isopropanol clathrate and the processes for the preparation of pure azithromycin monohydrate isopropanol clathrate.

Previously known forms of azithromycin (anhydrous, monohydrate, and dihydrate) may serve as the starting material in the present, all of which are commercially available.

According to this invention, azithromycin monohydrate isopropanol clathrate contains three molecules of isopropanol for every ten molecules of azithromycin monohydrate.

The process comprises the dissolution of azithromycin in isopropanol to which water is added slowly while stirring, resulting in the precipitation of crystalline azithromycin monohydrate isopropanol clathrate. The volume of solvent used is such as to be sufficient to dissolve azithromycin. The addition of the water is carried out between 0° and 30° C. and preferably between 15° C. to 25° C. The product is filtered and washed with a mixture of water-isopropanol and dried under vacuum (1–10 mm Hg) at 50° C. to 60° C. for 12–24 hours to obtain azithromycin monohydrate isopropanol clathrate in high yields. Extension of vacuum drying does not reduce either the water content or the isopropanol content of azithromycin monohydrate isopropanol clathrate.

Elemental analysis, 1HNMR, 13C NMR, and IR spectroscopy, mass spectrometry, and powder x-ray diffraction and IR have identified the azithromycin monohydrate isopropanol clathrate produced according to the invention. FIGS. 1 to 4 show the differences between powder x-ray diffraction of anhydrous azithromycin, azithromycin monohydrate, azithromycin monohydrate isopropanol clathrate, and azithromycin dihydrate. Comparison of FIG. 3 with FIGS. 1,2 and 4 clearly shows the differences in the morphology of azithromycin monohydrate isopropanol clathrate with anhydrous azithromycin, azithromycin monohydrate and azithromycin dihydrate. These figures also indicate that azithromycin monohydrate isopropanol clathrate is free of azithromycin dihydrate.

Figure 1:
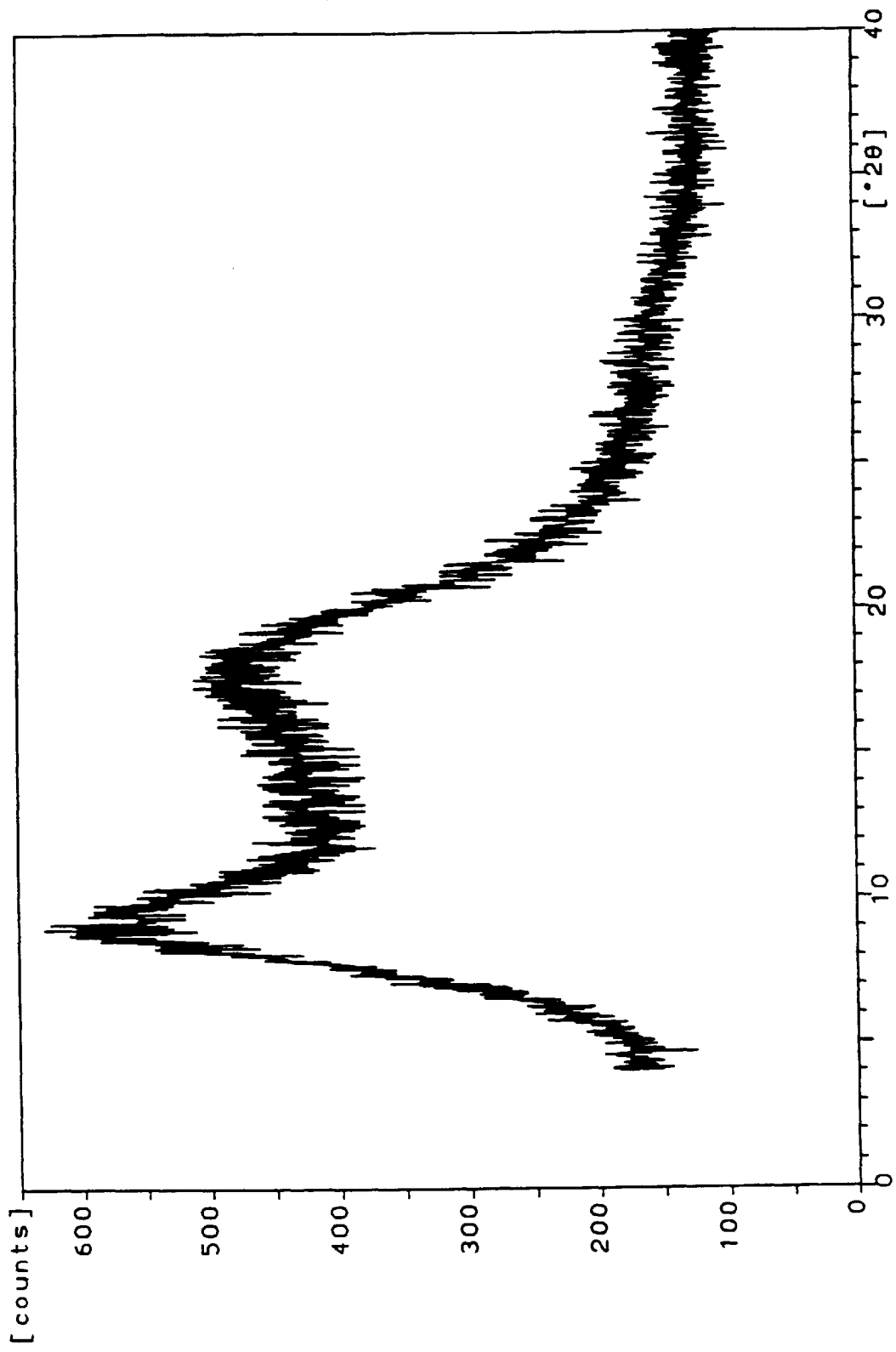
FIG. 1 is a powder X-Ray diffraction of anhydrous azithromycin.
Figure 2:
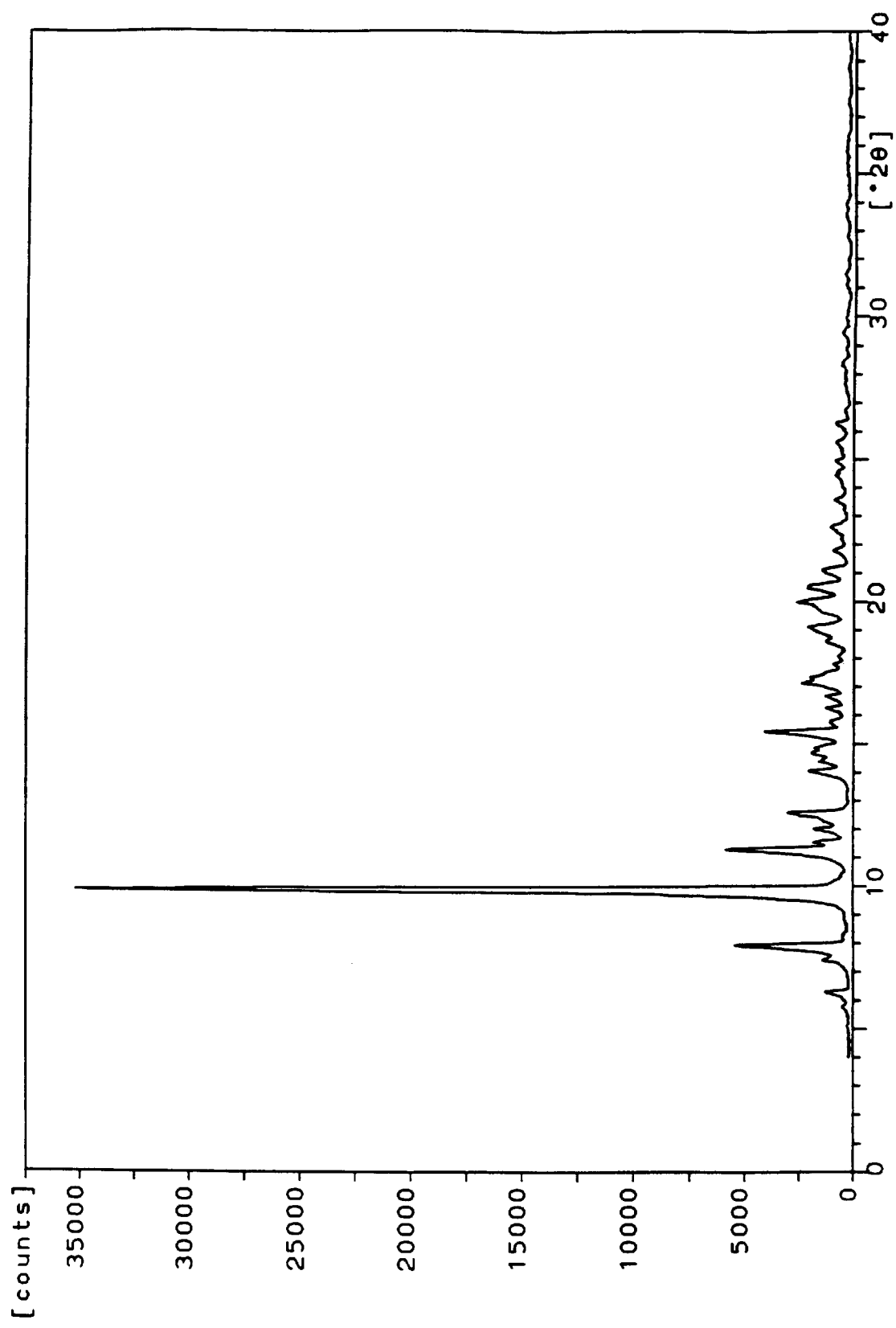
FIG. 2 is a powder X-Ray diffraction of azithromycin monohydrate.
Figure 3:
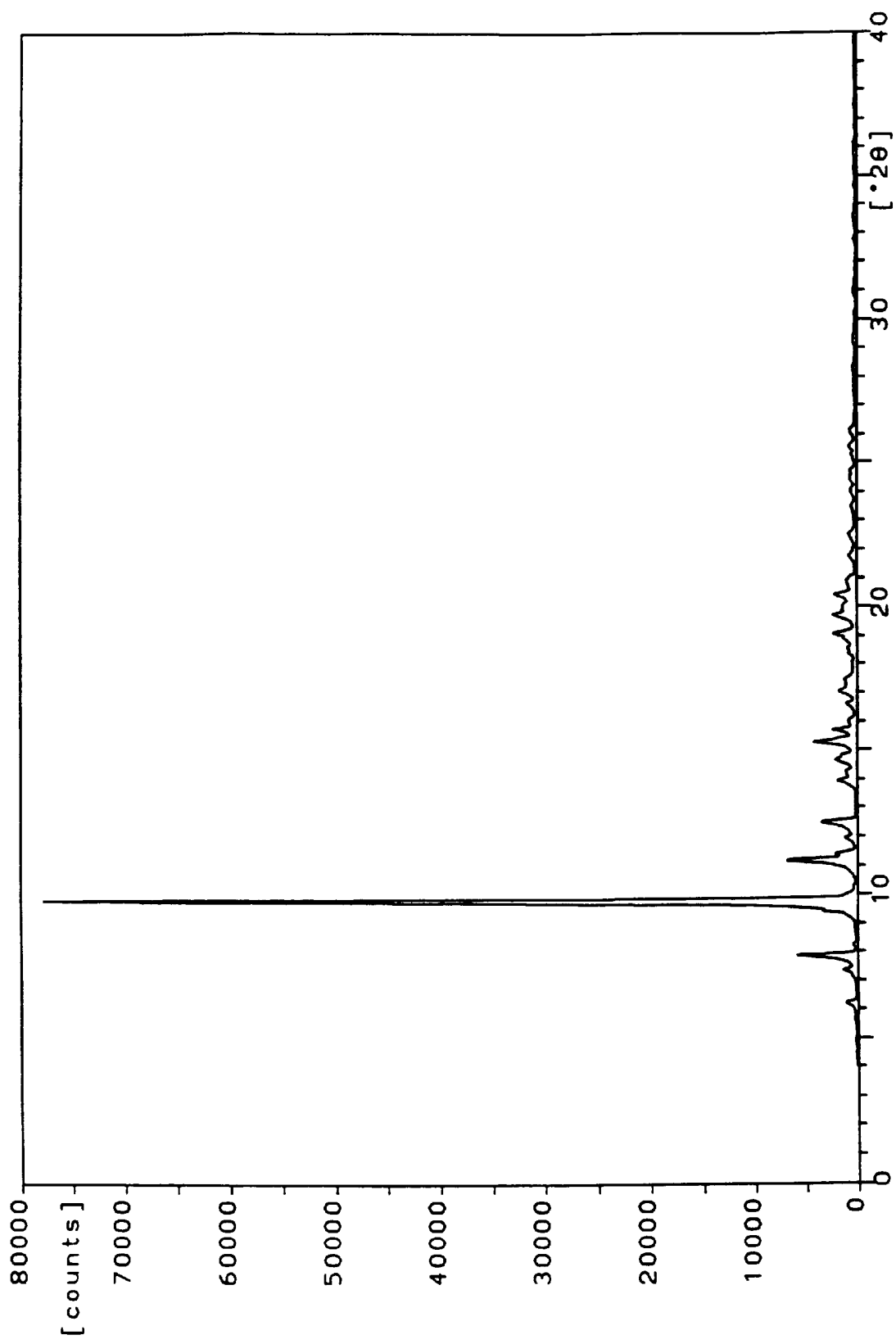
FIG. 3 is a powder X-Ray diffraction of azithromycin monohydrate isopropanol clathrate.
Figure 4:
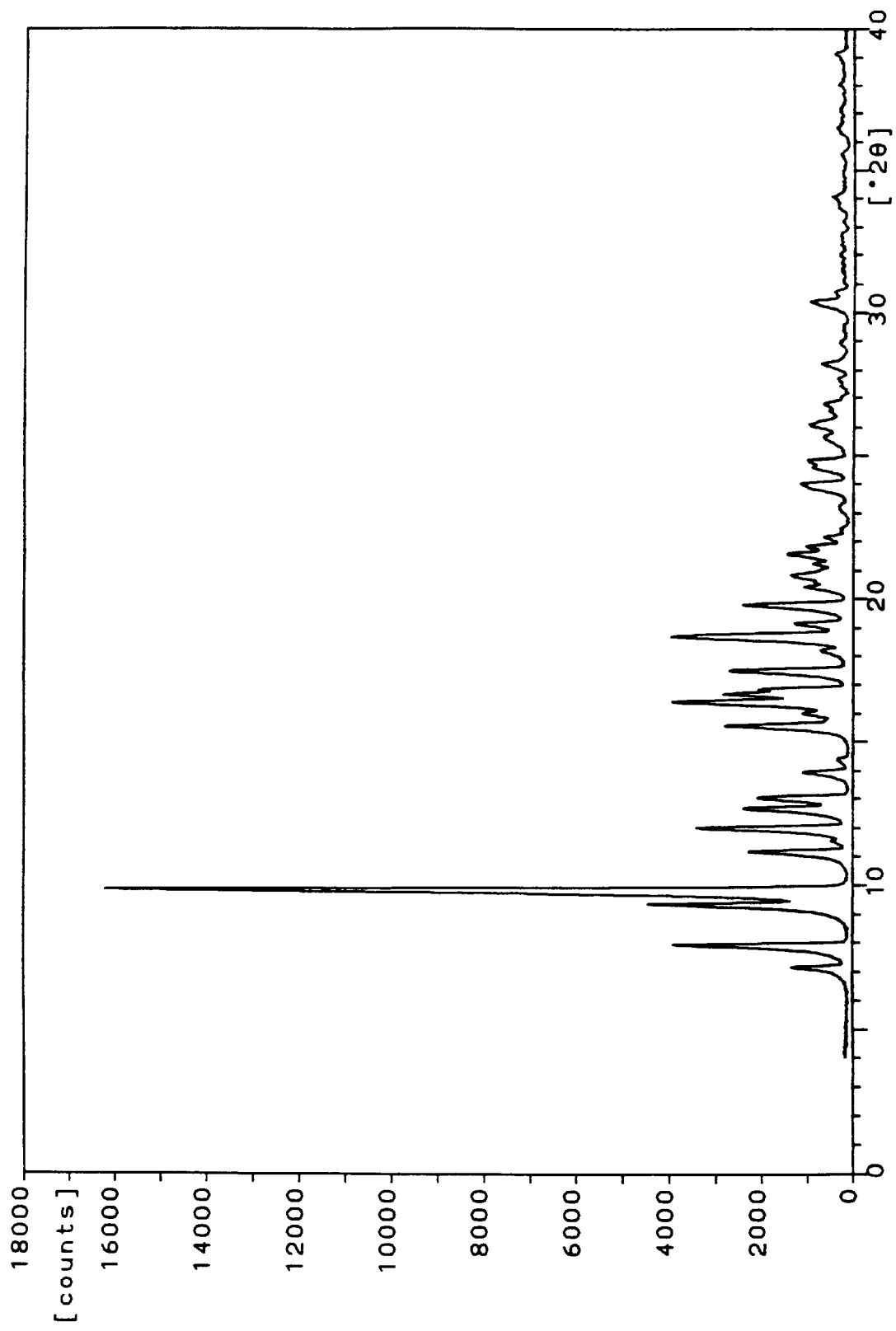
FIG. 4 is a powder X-Ray diffraction of azithromycin dihydrate.
Figure 5:
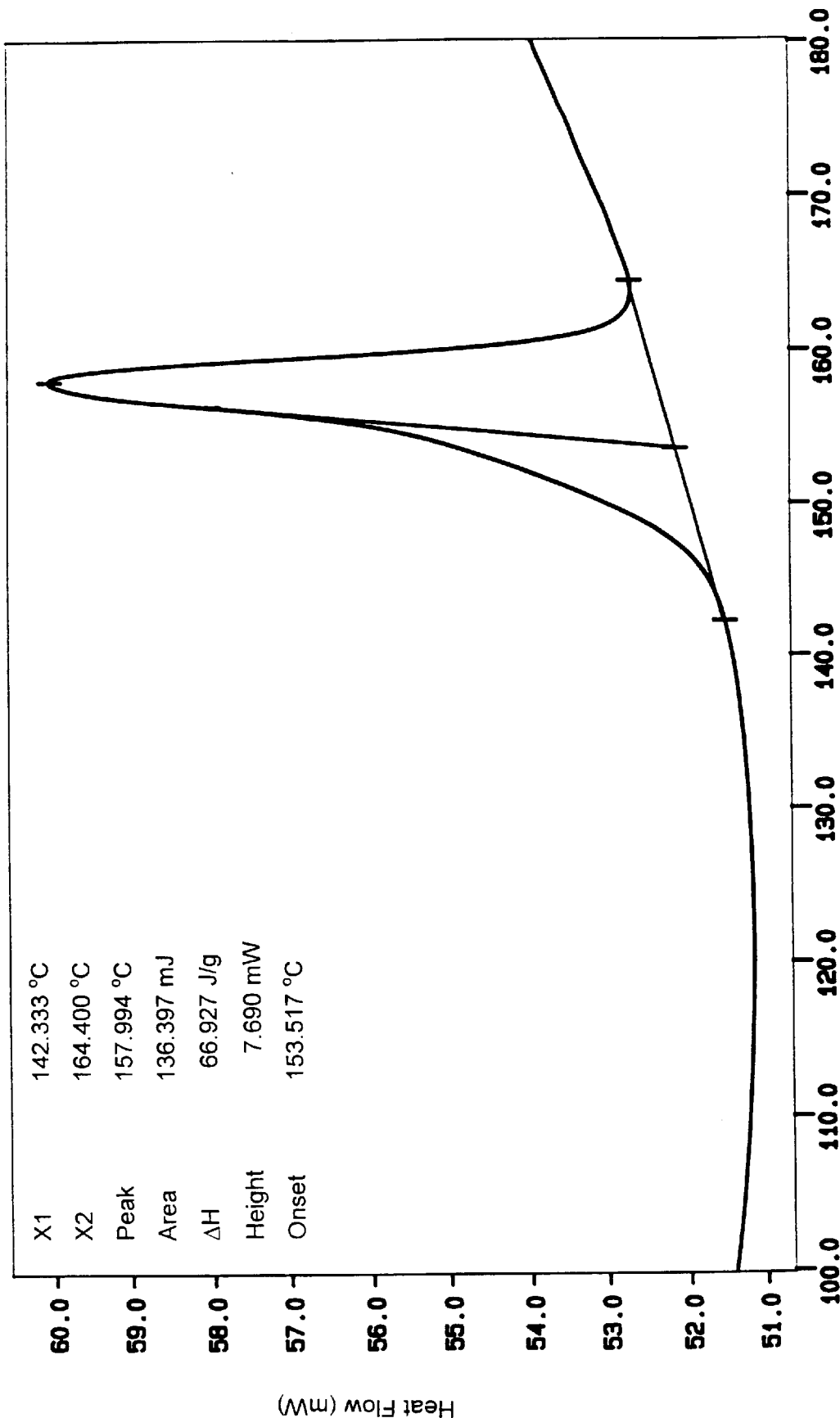
FIG. 5 is a DSC of azithromycin monohydrate.
Figure 6:
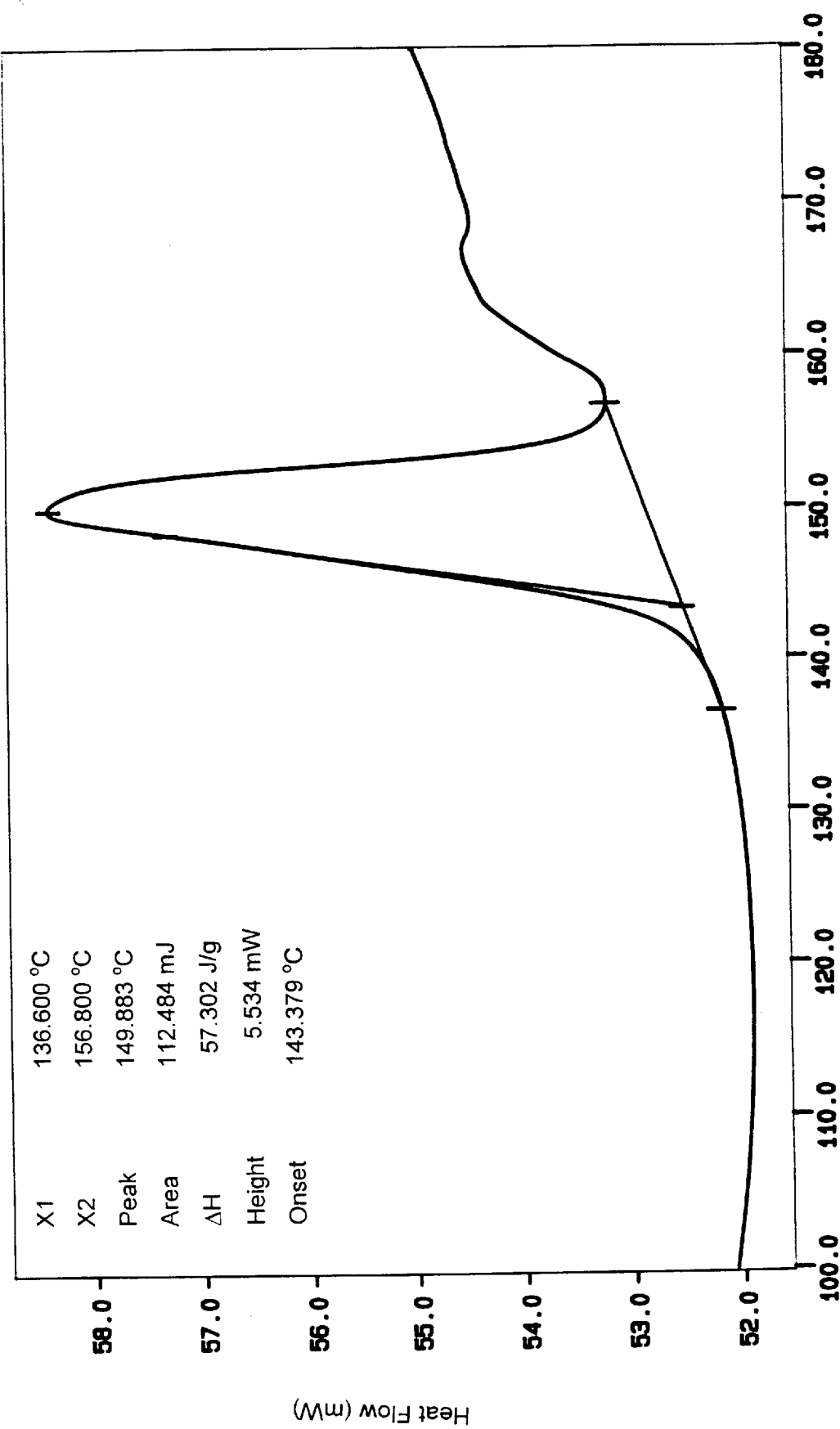
FIG. 6 is a DSC of azithromycin monohydrate isopropanol clathrate.

Differential Scanning Colorimetry (DSC) of azithromycin monohydrate (157.99° C.) and azithromycin monohydrate isopropanol clathrate (149.88° C.) are shown in FIGS. 5 and 6.

Figure 7:
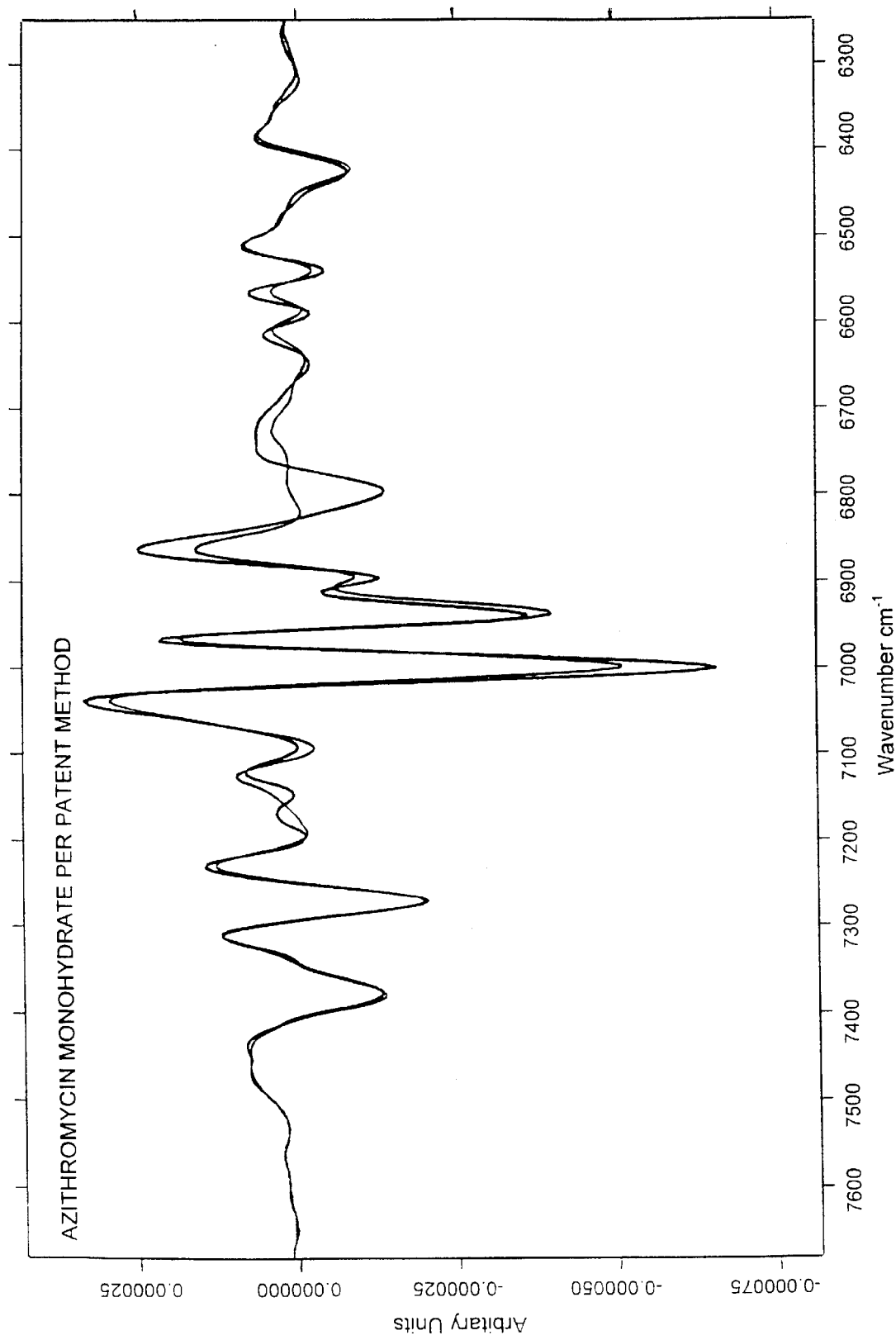
FIG. 7 is an IR spectrum of azithromycin monohydrate and azithromycin monohydrate isopropanol clathrate.

Near IR spectra of azithromycin monohydrate and azithromycin monohydrate isopropanol clathrate are shown in FIG. 7. The major difference is at 6800 cm$^{-1}$ at which the clathrate shows a medium absorption.

The water content of azithromycin monohydrate isopropanol clathrate was measured by the Karl-Fischer method and its isopropanol content was determined by gas chromatography.

X-RAY DIFFRACTION
Instrumental Parameters
Instrument: Philips PW3710 Based Diffractometer with APD Software Ver. 3.6

| | |
|---|---|
| Sample preparation | unground |
| Radiation: | CuKα$_1$(λ = 1.54056 Å) |
| Scanning Mode: | Step |
| Scanning Range (°2θ): | 4.0–40.0 |
| Step Size (°2θ): | 0.020 |
| Measuring Time (sec/step): | 1.20 |
| Holder type: | Phillips Standard |
| Operation | 40 KV × 40 mA |
| Power | 0.5° |
| Divergence Slit: | |
| Receiving Slit: | 0.2 mm |
| Scattering Slit: | 0.5° |

| Angle (°2θ) | D-value (Å) | Relative Intensity % |
|---|---|---|
| 4.985 | 17.712 | 0.2 |
| 5.605 | 15.754 | 0.3 |
| 6.205 | 14.232 | 1.3 |
| 7.350 | 12.017 | 1.7 |
| 7.855 | 11.246 | 7.5 |
| 8.240 | 10.721 | 0.4 |
| 8.830 | 10.006 | 0.3 |
| 9.400 | 9.401 | 4.1 |
| 9.790 | 9.027 | 100.0 |
| 10.245 | 8.627 | 0.4 |
| 11.165 | 7.918 | 8.8 |
| 11.365 | 7.779 | 2.5 |
| 11.935 | 7.409 | 1.4 |
| 12.495 | 7.078 | 4.3 |
| 13.955 | 6.341 | 2.2 |
| 14.250 | 6.210 | 1.2 |
| 14.645 | 6.044 | 2.6 |
| 14.810 | 5.977 | 1.8 |
| 15.270 | 5.798 | 5.3 |
| 15.700 | 5.640 | 2.9 |
| 15.990 | 5.538 | 0.9 |
| 16.595 | 5.338 | 1.1 |
| 17.040 | 5.199 | 2.1 |
| 17.450 | 5.078 | 1.5 |
| 18.035 | 4.915 | 0.5 |
| 18.375 | 4.824 | 1.0 |
| 18.540 | 4.782 | 1.0 |
| 19.060 | 4.653 | 2.8 |
| 19.670 | 4.510 | 2.8 |
| 19.995 | 4.437 | 1.7 |
| 20.425 | 4.345 | 2.7 |
| 20.885 | 4.250 | 1.1 |
| 21.030 | 4.221 | 0.8 |
| 21.740 | 4.085 | 0.8 |
| 22.540 | 3.941 | 0.8 |
| 23.470 | 3.787 | 0.5 |
| 24.125 | 3.686 | 0.6 |
| 24.475 | 3.634 | 0.7 |
| 24.705 | 3.601 | 0.7 |
| 25.245 | 3.525 | 0.6 |
| 25.510 | 3.489 | 0.9 |
| 26.145 | 3.406 | 0.8 |
| 26.510 | 3.360 | 0.2 |
| 28.320 | 3.145 | 0.3 |
| 29.200 | 3.056 | 0.3 |
| 29.410 | 3.035 | 0.3 |
| 29.825 | 2.993 | 0.2 |
| 30.170 | 2.960 | 0.2 |
| 32.750 | 2.732 | 0.4 |
| 33.565 | 2.668 | 0.4 |
| 34.640 | 2.587 | 0.2 |
| 35.295 | 2.541 | 0.3 |
| 36.135 | 2.484 | 0.3 |
| 37.490 | 2.397 | 0.2 |
| 39.710 | 2.268 | 0.2 |

The invention will be more fully understood by the following examples, which illustrate the present invention, but are not to be considered limiting to the scope of the invention.

EXAMPLE 1

Anhydrous azithromycin (1 kg) is dissolved in isopropanol (2.8 kg) by warming. The solution is stirred vigorously and water (4.35 kg) is added slowly over a 1-hour period. The mixture is cooled to 20° C. and stirred for an additional 6 hours at this temperature. The resulting product is filtered and washed with a 40:60 mixture of isopropanol-water. The cake was then dried vacuum (6 to 10 mm Hg) at 50° C. for 12 hours. Yield 0.88 kg (88%).

EXAMPLE 2

Azithromycin monohydrate (1 kg) is dissolved in isopropanol (2.8 kg) by warming. The solution is stirred vigorously and water (4.35 kg) is added slowly over a 1-hour period. The mixture is cooled to 20° C. and stirred for an additional 6 hours at this temperature. The resulting product is filtered and washed with a 40:60 mixture of isopropanol-water. The cake was then dried vacuum (6 to 10 mm Hg) at 50° C. for 12 hours. Yield 0.88 kg (88%).

EXAMPLE 3

Azithromycin dihydrate (1 kg) is dissolved in isopropanol (2.8 kg) by warming. The solution is stirred vigorously and water (4.35 kg) is added slowly over a 1-hour period. The mixture is cooled to 20° C. and stirred for an additional 6 hours at this temperature. The resulting product is filtered and washed with a 40:60 mixture of isopropanol-water. The cake was then dried vacuum (6 to 10 mm Hg) at 50° C. for 12 hours. Yield 0.88 kg (88%).

What is claimed is:

1. A compound of formula II:

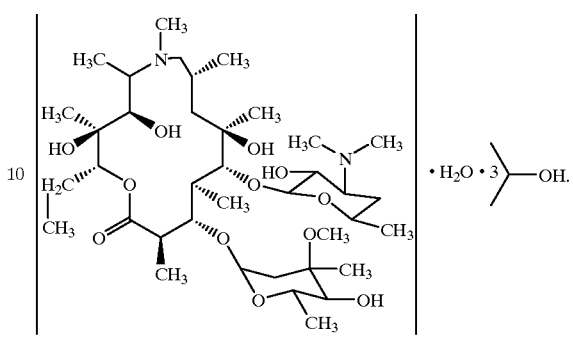

2. A process for the preparation of azithromycin monohydrate isopropanol clathrate which comprises the steps of:

(a) dissolving azithromycin in isopropanol and slowly adding water to the resulting solution so that a precipitate of crystalline azithromycin monohydrate isopropanol clathrate is formed;

(b) filtering and washing the product resulting from step (a) with a mixture of isopropanol and water; and (c) vacuum drying the product resulting from step (b).

3. The process of claim 2 wherein the dissolution of crystalline azithromycin is carried out in a volume of solvent only sufficient to dissolve the azithromycin.

4. The process of claim 2 wherein water is added over a period of one hour.

5. The process of claim 2 wherein the addition of water to the resulting solution is carried out between 0° C. to 30° C.

6. The process of claim 5 wherein the addition of water is carried between 15° C. to 25° C.

7. The process of claim 2 wherein vacuum drying is carried out at a temperature of 50° C. to 60° C.

8. The process of claim 2 wherein the vacuum drying is carried out under 6 to 10 mm Hg.

9. A process for the preparation of azithromycin monohydrate isopropanol clathrate characterised by the following x-ray powder diffraction pattern expressed in terms of "D" spacings and Relative Intensity:

| Angle (°2θ) | D-value (Å) | Relative Intensity % |
| --- | --- | --- |
| 4.985 | 17.712 | 0.2 |
| 5.605 | 15.754 | 0.3 |
| 6.205 | 14.232 | 1.3 |
| 7.350 | 12.017 | 1.7 |
| 7.855 | 11.246 | 7.5 |
| 8.240 | 10.721 | 0.4 |
| 8.830 | 10.006 | 0.3 |
| 9.400 | 9.401 | 4.1 |
| 9.790 | 9.027 | 100.0 |
| 10.245 | 6.627 | 0.4 |
| 11.165 | 7.918 | 8.8 |
| 11.365 | 7.779 | 2.5 |
| 11.935 | 7.409 | 1.4 |
| 12.495 | 7.078 | 4.3 |
| 13.955 | 6.341 | 2.2 |
| 14.250 | 6.210 | 1.2 |
| 14.645 | 6.044 | 2.6 |
| 14.810 | 5.977 | 1.8 |
| 15.270 | 5.798 | 5.3 |
| 15.700 | 5.640 | 2.9 |
| 15.990 | 5.538 | 0.9 |
| 16.595 | 5.338 | 1.1 |
| 17.040 | 5.199 | 2.1 |
| 17.450 | 5.078 | 1.5 |
| 18.035 | 4.915 | 0.5 |
| 18.375 | 4.824 | 1.0 |
| 18.540 | 4.782 | 1.0 |
| 19.060 | 4.653 | 2.8 |
| 19.670 | 4.510 | 2.8 |
| 19.995 | 4.437 | 1.7 |
| 20.425 | 4.345 | 2.7 |
| 20.885 | 4.150 | 1.1 |
| 21.030 | 4.221 | 0.8 |
| 21.740 | 4.085 | 0.8 |
| 22.540 | 3.941 | 0.8 |
| 23.470 | 3.787 | 0.5 |
| 24.125 | 3.686 | 0.6 |
| 24.475 | 3.634 | 0.7 |
| 24.705 | 3.601 | 0.7 |
| 25.245 | 3.525 | 0.6 |
| 25.510 | 3.489 | 0.9 |
| 26.145 | 3.406 | 0.8 |
| 26.510 | 3.360 | 0.2 |
| 28.320 | 3.145 | 0.3 |
| 29.200 | 3.056 | 0.3 |
| 29.410 | 3.035 | 0.3 |
| 29.825 | 2.993 | 0.2 |
| 30.170 | 2.960 | 0.2 |
| 32.750 | 2.732 | 0.4 |
| 33.565 | 2.668 | 0.4 |
| 34.640 | 2.587 | 0.2 |
| 35.295 | 2.541 | 0.3 |
| 36.135 | 2.484 | 0.3 |
| 37.490 | 2.397 | 0.2 |
| 39.710 | 2.268 | 0.2 | which comprises the steps of:

(a) dissolving azithromycin in isopropanol and slowly adding water to the resulting solution so that a precipitate of crystalline azithromycin monohydrate isopropanol clathrate is formed;

(b) filtering and washing the product resulting from step (a) with a mixture of isopropanol and water; and (c) vacuum drying the product resulting from step (b).

* * * * *

UNITED STATES PATENT AND TRADEMARK OFFICE
CERTIFICATE OF CORRECTION

PATENT NO. : 6,245,903 B1
DATED : June 12, 2001
INVENTOR(S) : Khashayar Karimian and Mehrnoush Motamedi It is certified that error appears in the above-identified patent and that said Letters Patent is hereby corrected as shown below:

Column 3,
Line 1, in the "BACKGROUND OF THE INVENTION", the current figure should be replaced with the following figure:

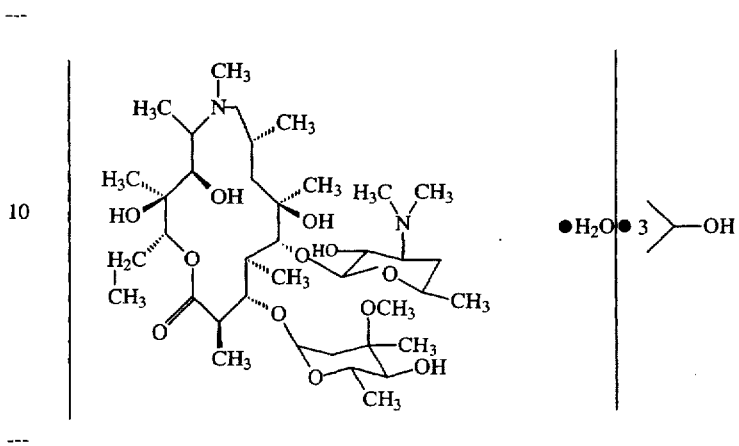

Column 4,
Line 1, in the "BRIEF DESCRIPTION OF THE INVENTION", the current figure should be replaced with the following figure:

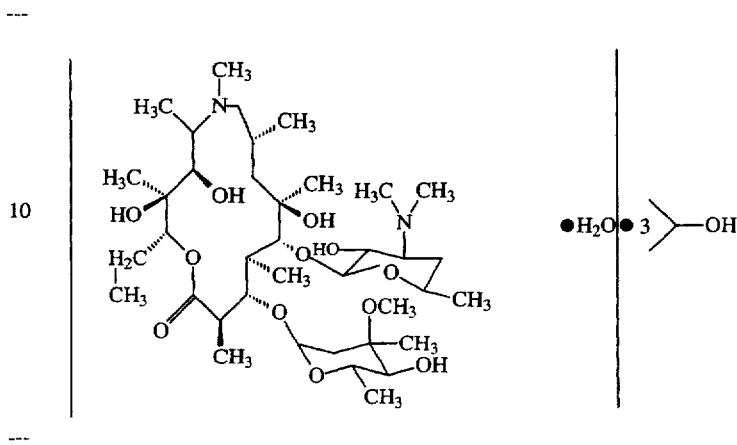

UNITED STATES PATENT AND TRADEMARK OFFICE
CERTIFICATE OF CORRECTION

PATENT NO. : 6,245,903 B1
DATED : June 12, 2001
INVENTOR(S) : Khashayar Karimian and Mehrnoush Motamedi Page 2 of 2

It is certified that error appears in the above-identified patent and that said Letters Patent is hereby corrected as shown below:

Column 7,
Line 20, the current figure should be replaced with the following figure:

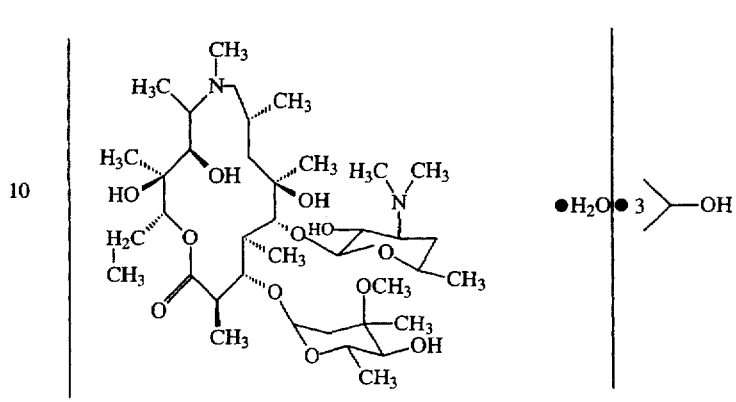

Signed and Sealed this

Thirtieth Day of April, 2002

Attest:

JAMES E. ROGAN
Director of the United States Patent and Trademark Office

Attesting Officer